United States Patent [19]

Rovnyak

[11] 4,221,804
[45] Sep. 9, 1980

[54] MERCAPTOACYLDIHYDROPYRAZOLE CARBOXYLIC ACID DERIVATIVES

[75] Inventor: George C. Rovnyak, Hopewell, N.J.

[73] Assignee: E. R. Squibb & Sons, Inc., Princeton, N.J.

[21] Appl. No.: 79,291

[22] Filed: Sep. 27, 1979

Related U.S. Application Data

[62] Division of Ser. No. 18,548, Mar. 8, 1979.

[51] Int. Cl.³ ................. C07D 231/06; A61K 31/415
[52] U.S. Cl. .................................. 424/273 P; 548/379
[58] Field of Search ..................... 548/379; 424/273 P

[56] References Cited

U.S. PATENT DOCUMENTS

| 4,105,776 | 8/1978 | Ondetti et al. | 424/274 |
| 4,129,566 | 12/1978 | Ondett et al. | 546/326 |

FOREIGN PATENT DOCUMENTS

| 861454 | 6/1978 | Belgium | 546/326 |

Primary Examiner—Alan L. Rotman
Assistant Examiner—Natalia Harkaway

Attorney, Agent, or Firm—Lawrence S. Levinson, Donald J. Barrack

[57] ABSTRACT

Hypertension can be treated using compounds having the formula

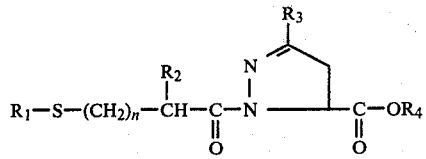

or a basic salt thereof, wherein
$R_1$ is hydrogen, alkyl, aryl, arylalkyl or

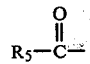

wherein
$R_5$ is alkyl or aryl;
$R_2$ is hydrogen or alkyl;
$R_3$ is aryl;
$R_4$ is hydrogen, alkyl or arylalkyl and
n is 0, 1 or 2.

14 Claims, No Drawings

MERCAPTOACYLDIHYDROPYRAZOLE CARBOXYLIC ACID DERIVATIVES

This is a division of application Ser. No. 018,548 pending, filed Mar. 8, 1979.

RELATED APPLICATIONS

U.S. patent application, Ser. No. 18,547, filed Mar. 8, 1979, discloses mercaptoacylpyrazolidinone carboxylic acid derivatives.

BACKGROUND OF THE INVENTION

U.S. Pat. No. 4,105,776, issued Aug. 8, 1978, describes a group of thioalkanoyl derivatives of azetidine-, or pyrrolidine- and piperidinecarboxylic acid compounds having the structural formula $$R_a-S-(CH)_n-CH-C-N-CH-C-R_e$$

with substituents $R_b$, $R_c$, $R_d$ (on $H_2C-(CH)_m$), and carbonyl groups.

wherein the symbols can be, inter alia, as follows: $R_a$ can be hydrogen, lower alkyl, phenyl, substituted phenyl, phenyl-lower alkyl, lower alkyl-$\overset{O}{\overset{\|}{C}}-$, phenyl-$\overset{O}{\overset{\|}{C}}-$ or phenyl-lower alkyl-$\overset{O}{\overset{\|}{C}}-$, $R_b$ can be hydrogen, $R_c$ can be hydrogen or lower alkyl, $R_d$ can be hydrogen, hydroxy or lower alkyl, $R_e$ can be hydroxy, —NH$_2$ or lower alkoxy, n can be 0, 1 or 2 and m can be 1, 2 or 3.

U.S. Pat. No. 4,129,566, issued Dec. 12, 1978, describes derivatives of dehydrocyclicimino acids having the structural formula $$R_f-S-(CH_2)_n-CH-C-N\cdots COOR_g$$

wherein the symbols can be, inter alia, as follows: $R_c$, $R_f$ and $R_g$ can each be hydrogen or lower alkyl and n can be 0 or 1.

Belgian Pat. No. 861,454, published June 2, 1978, describes compounds having the structural formula $$R_h-S-(CH_2)_p-CH-C-N-CH-C-R_L$$

with substituents $R_i$, $R_j$, $R_k$, X.

wherein the symbols can be, inter alia as follows: $R_h$ can be hydrogen, lower alkanoyl or benzoyl, $R_i$, $R_j$ and $R_k$ can each be hydrogen or lower alkyl, $R_L$ can be hydroxy or lower alkoxy, m can be 1, 2 or 3, n can be 0, 1 or 2 and m+n can be 2 or 3, p can be 0 or 1 and X can be O, S, SO or SO$_2$, m being 2 and n being 1 when X is O.

The compounds set forth above are disclosed as being useful as inhibitors of the conversion of the decapeptide angiotensin I to angiotensin II, and are, therefore, useful in reducing or relieving angiotensin related hypertension.

BRIEF DESCRIPTION OF THE INVENTION

Compounds having the formula $$R_1-S-(CH_2)_n-CH-C-N\cdots C-OR_4 \quad (I)$$

with substituents $R_2$, $R_3$.

and basic salts thereof, have hypotensive activity. In formula I, and throughout the specification, the symbols are as defined below.

$R_1$ is hydrogen, alkyl, aryl, arylalkyl or $$R_5-\overset{O}{\overset{\|}{C}}-$$

wherein $R_5$ is alkyl or aryl;
$R_2$ is hydrogen or alkyl;
$R_3$ is aryl;
$R_4$ is hydrogen, alkyl or arylalkyl; and
n is 0, 1 or 2.

The term "aryl", as used throughout the specification either by itself or as part of a larger group, refers to phenyl or phenyl substituted with one, two or three halogen, alkyl, alkoxy, hydroxy, $$\text{alkyl}-\overset{O}{\overset{\|}{C}}-,$$

nitro, amino, alkylamino, dialkylamino, trifluoromethyl, cyano or carboxyl groups. Phenyl is the preferred aryl group.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are chlorine and bromine.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin coverting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 50 mg. per kilogram of body weight per day is appropriate to reduce blood pressure. The substance is preferably administered orally, but parenteral routes such as the subcutaneous, intramuscular, intravenous or interperitoneal routes can also be employed.

The compounds of formula I can be formulated for use in the reduction of blood pressure in compositions such as tablets, capsules or elixirs for oral administration or in sterile solutions or suspensions for patenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared by reacting a 4,5-dihydro-3-aryl-1H-pyrazole-5-carboxylic acid having the formula

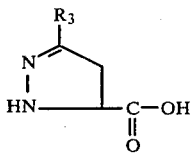
II with a mercaptoacyl halide having the formula

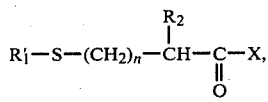
III wherein $R_1'$ is alkyl, aryl, arylalkyl,

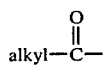

or

and X is chlorine or bromine, to obtain the corresponding products of formula I wherein $R_1$ is other than hydrogen and $R_4$ is hydrogen; i.e., compounds having the formula

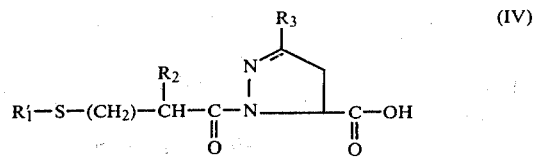
(IV)

The reaction is preferably run in a two phase solvent system such as water/ether or water/ethyl acetate, in the presence of a base such as an alkali metal hydroxide or alkali metal carbonate. While reaction conditions are not critical, more favorable yields will be obtained if the reaction is run within the following parameters. The ratio of pyrazole derivative (formula II) to mercaptoacyl halide (formula III) will preferably be within the range of 1:1 to 1:2, most preferably within the range of 1:1 to 1:1.2. The temperature of the reaction is preferably maintained at about 0°–25° C., most preferably 0°–5° C. Additional base should be added as needed to maintain the pH of the reaction mixture between about 7.0 and 8.5.

Alternatively, a compound of formula IV can be obtained by reacting a 4,5-dihydro-3-aryl-1H-pyrazole-5-carboxylic acid of formula II with a mixed anhydride in place of the mercaptoacyl halide of formula III.

The compounds of formula I wherein $R_1$ and $R_4$ are both hydrogen can be prepared by deacylation of the corresponding compounds of formula IV wherein $R_1'$ is

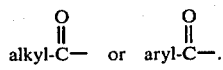

Hydrolysis of the thioacyl group can be accomplished by treatment with aqueous base, e.g., ammonium hydroxide or an alkali metal hydroxide.

The compounds of formula I wherein $R_4$ is alkyl or arylalkyl can be obtained by treating the corresponding acid of formula I with the appropriate diazoalkane or with the appropriate alcohol in the presence of a dehydrating agent such as dicyclohexylcarbodiimide. Alternatively, an acid of formula I can be converted first to an acid halide and then reacted with the appropriate alcohol in the presence of an acid acceptor, e.g., an organic base such as triethylamine.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The 4,5-dihydro-3-aryl-1H-pyrazole-5-carboxylic acids of formula II can be prepared using the procedure described in *Ann. Pharm. Fr.*, 36, 67 (1978). As described therein, an aroylacrylic acid derivative can be treated with one equivalent each of hydrazine and potassium hydroxide in aqueous ethanol at reflux for two hours, followed by acidification to obtain a starting compound of formula II.

The mercaptoacyl halide derivatives of formula III are prepared by methods known in the art; see, for example, Arkiv. Kimi, Mineral. Geol., 14A (7), 1940; J, Chem. Soc. 2016; J.A.C.S., 69, 2328 (1947); and J.A.C.S. 69, 2334 (1947).

The compounds of formula I each contains at least one asymmetric carbon and accordingly exist in stereoisomeric forms or in racemic mixtures thereof. The above described synthesis can utilize the racemate or one of the enantiomers as starting material. When the racemic starting material is used in the synthetic procedure, the stereoisomers obtained in the product can be separated by conventional fractional crystallization of the diastereomeric salt mixture formed, e.g., with an optically active amine. It is theorized that the activity of the racemic products is due mostly to the L-isomer with respect fo the carbon of the amino acid, and this isomer is accordingly preferred.

The following examples are specific embodiments of this invention.

EXAMPLE 1

DL-4,5-Dihydro-1-[3-(acetylthio)-1-oxopropyl]-3-phenyl-1H-pyrazole-5-carboxylic acid (A) 4,5-Dihydro-3-phenyl-1H-pyrazole-5-carboxylic acid A mixture of 10.0 g of 3-benzoylacrylic acid, 1.8 g of hydrazine, and 3.7 g of potassium hydroxide in 30 ml. of aqueous ethanol (1:1) is stirred and heated at reflux for 2 hours. The cooled solution is treated with 5 ml of concentrated hydrochloric acid to pH 4.0 to precipitate 7.1 g of solid, melting point 180°–182° C. This material is dissolved in 40 ml of warm dimethylformamide and treated wit 140 ml of methanol to crystallize 3.9 g of the title compound, melting point 199°–201° C.

Anal. Calcd. for $C_{10}H_{10}N_2O_2$: C, 63.14; H, 5.29; N, 14.73. Found: C, 63.06; H, 5.40; N, 14.71.

(B) DL-4,5-Dihydro-1-[3-(acethylthio)-1-oxopropyl]-3-phenyl-1H-pyrazole-5-carboxylic acid A suspension of 8.0 g of 4,5-dihydro-3-phenyl-1H-pyrazole-5-carboxylic acid in 200 ml of distilled water is treated slowly with 2.6 g of sodium carbonate. The solution is layered with 50 ml of ethyl acetate, cooled to 5° C. and treated with 7.0 g of 3-(acetylthio)propionyl chloride in 10 ml of ethyl acetate. The pH of the reaction mixture is maintained at 7.5–8.0 by the addition of concentrated sodium carbonate solution. The mixture is stirred at room temperature for 30 minutes. The ethyl acetate layer is then discarded and the aqueous layer is washed twice with fresh ethyl acetate. Using 6N hydrochloric acid, the pH of the aqueous layer is adjusted to 2.5 and then it is extracted with two 100ml portions of ethyl acetate. The combined extracts are dried over magnesium sulfate and concentrated to a point where precipitation begins. Cooling affords 10.6g of the title compound, melting point 137°–139° C.

Anal. calcd. for $C_{15}H_{16}N_2O_4S$: C, 56.23; H, 5.03; N, 8.74; S, 10.00.
Found: C, 56.20; H, 5.18; N, 8.68; S, 9.90.

EXAMPLE 2

DL-4,5-Dihydro-1-(3-mercapto-1-oxopropyl)-3-phenyl-1H-pyrazole-5-carboxylic acid DL-4,5-Dihydro-1-[3-(acetylthio)-1-oxopropyl]-3-phenyl-1H-pyrazole-5-carboxylic acid (6.0g) is treated in an argon atmosphere with 40ml of a cold solution of 6.5N ammonium hydroxide. After 30 minutes at room temperature, the solution is washed with ethyl acetate, treated with concentrated hydrochloric acid to pH 2.5 and extracted with ethyl acetate. The extract is dried over magnesium sulfate and concentrated in vacuo to an oil. Trituration of the oil with ether yields 3.6g of the title compound, melting point 118°–120° C.

Anal. calcd. for $C_{13}H_{14}N_2O_3S$: C, 56.09; H, 5.06; N, 10.06; S, 11.51.
Found: C, 55.82 H, 5.23; N, 10.04; S, 11.45.

EXAMPLE 3

DL-3-(4-Chlorophenyl)-4,5-dihydro-1-[3-(acetylthio)-1-oxopropyl]-1H-pyrazole-5-carboxylic acid (A) 4-(4-Chlorophenyl)-4-oxo-2-butenoic acid A mixture of 30.0 g. of chloroacetophenone and 18.0 g. of glyoxylic acid hydrate is heated with stirring in an oil bath at 165°–170° C. for 40 minutes. The cooled mixture is triturated with acetonitrile to give 17.4 g. of product, melting point 158°–160° C.

(B) 3-(4-Chlorophenyl)-4,5-dihydro-1H-pyrazole-5-carboxylic acid

To a solution of 20.0 g. of 4-(4-chlorophenyl)-4-oxo-2-butenoic acid in 200 ml. of methanol containing 6.4 g. of potassium hydroxide is added 4.0 g. of anhydrous hydrazine. After heating at reflux temperature for three hours, the solution is concentrated to one-half volume and 50 ml. of water is added. The pH is adjusted to 2.0 with 25 ml. of 6N hydrochloric acid, yielding 16.9 g. of a precipitate, melting point 148°–150° C. Recrystallization from ethanol (filtered hot to remove insoluble material) gives 7.8 g. of product, melting point 151°–153° C.

(C) DL-3-(4-Chlorophenyl)-4,5-dihydro-1-[3-(acetylthio)-1-oxopropyl]-1H-pyrazole-5-carboxylic acid Using the procedure described in Example 1B, but starting with 8.1 g. of 3-(4-chlorophenyl)-4,5-dihydro-1H-pyrazole-5-carboxylic acid and 6.0 g. of 3-(acetylthio) propionyl chloride there is obtained 10.0 g. of product, melting point 151°–153° C., recrystallized from acetonitrile.

EXAMPLE 4

D,L-3-(4-Chlorophenyl)-4,5-dihydro-1-(3-mercapto-1-oxopropyl)-1H-pyrazole-5-carboxylic acid Using the procedure described in Example 2, but starting with 5.0 g. of D,L-3-(4-chlorophenyl)-4,5-dihydro-1-[3-(acetylthio)-1-oxopropyl]-1H-pyrazole-5-carboxylic acid there is obtained 2.9 g. of product, melting point 178°–180° C. recrystallized from ethanol.

Anal. Calc'd. for $C_{13}H_{13}ClN_2O_2S$ C, 49.92; H, 4.18; N, 8.95; Cl, 11.33; S, 10.25.

Found: C, 50.00; H, 4.19; N, 8.93; Cl, 11.30; S, 10.47.

EXAMPLE 5

D,L-3-(4-Methoxyphenyl)-4,5-dihydro-1-[3-(acetylthio)-1-oxopropyl]-1H-pyrazole-5-carboxylic acid (A) 4-(4-Methoxyphenyl)-4-oxo-2-butenoic acid A mixture of 49.0 g. of 4-methoxyacetophenone and 40.0 g. of glyoxylic acid hydrate is heated in an oil bath at 150°–155° C. for 2 hours. The cooled mixture is triturated first with acetonitrile and then with isopropyl ether to give 16.5 g. of product, melting point 131°–133° C.

(B) 3-(4-Methoxyphenyl)-4,5-dihydro-1H-pyrazole-5-carboxylic acid

Using the procedure described in Example 3B, but starting with 16.5 g. of 4-(4-methoxyphenyl)-4-oxo-2-butenoic acid, 5.3 g. of potassium hydroxide and 4.0 g. of anhydrous hydrazine, there is obtained 18.6 g. of product, melting point 171°–173° C.

(C) D,L-3-(4-Methoxyphenyl)-4,5-dihydro-1-[3-(acetylthio)-1-oxopropyl]-1H-pyrazole-5-carboxylic acid Using the procedure described in Example 1B, but starting with 5.0 g. of 3-(4-methoxylphenyl)-4,5-dihydro-1H-pyrazole-5-carboxylic acid and 3.8 g. of 3-(acetylthio) propinonyl chloride, there is obtained 6.2 g. (80%) of product, melting point 134°–136° C., recrystallized from ethanol.

EXAMPLE 6

D,L-3-(4-Methoxyphenyl)-4,5-dihydro-1-(3-mercapto-1-oxopropyl)-1H-pyrazole-5-carboxylic acid Using the procedure described in Example 2, but starting with 6.2 g. of D,L-3-(4-methoxyphenyl)-4,5-dihydro-1-[3-(acetylthio)-1-oxopropyl]-1H-pyrazole-5-carboxylic acid, there is obtained 2.7 g. of product, melting point 138°–140° C., recrystallized from ethanol.

Anal. Calc'd. for $C_{14}H_{16}N_2O_4S$: C, 54.52; H, 5.23; N, 9.08; S, 10.39.
Found: C, 54.67; H, 5.13; N, 9.13; S, 10.42.

EXAMPLE 7

D,L-3-(4-Fluorophenyl)-4,5-dihydro-1-[3-(acetylthio)-1-oxopropyl]-1H- pyrazole-5-carboxylic acid (A) 4-(4-Fluorophenyl)-4-oxo-2-butenoic acid A mixture of 43.1 g. of 4-fluoroacetophenone and 29.1 g. of glyoxylic acid hydrate is heated with stirring in an oil bath at 145°–150° C. for 45 minutes. The cooled mixture is dissolved in chloroform, washed with water and concentrated. Trituration of the residue with isopropyl ether gives 18.2 g. of product, melting point 132°–134° C.

(B) 3-(4-Fluorophenyl)-4,5-dihydro-1H-pyrazole-5-carboxylic acid

Using the method described in Example 3B but starting with 10.0 g. of 4-(4-fluorophenyl)-4-oxo-2-butenoic acid, 3.5 g. of potassium hydroxide and 2.0 g. of anhydrous hydrazine, there is obtained 6.2 g. of product, melting point 163°–165° C., recrystalized from ethanol.

(C) D,L-3-(4-Fluorophenyl)-4,5-dihydro-1-[3-(acetylthio)-1-oxopropyl]-1H-pyrazole-5-carboxylic acid Using the procedure described in Example 1B, but starting with 6.2 g. of 3-(4-fluorophenyl)-4,5-dihydro-1H-pyrazole-5-carboxylic acid and 4.8 g. of 3-(acetylthio) propionyl chloride, there is obtained 8.0 g. of product, melting point 156°–158° C., recrystallized from ethanol.

EXAMPLE 8

D,L-3-(4-Fluorophenyl)-4,5-dihydro-1-(3-mercapto-1-oxopropyl)-1H-pyrazole-5-carboxylic acid Using the procedure described in Example 2, but starting with 8.0 g. of D,L-3-(4-fluorophenyl)-4,5-dihydro-1-[3-(acetylthio)-1-oxopropyl]-1H-pyrazole-5-carboxylic acid, there is obtained 4.9 g. of product, melting point 155°–157° C., recrystallized from ethanol.

Anal. Calc'd. for $C_{13}H_{13}FN_2O_3S$: C, 52.69; H, 4.42; N, 9.45; S, 10.81; F, 6.41.
Found: C, 52.70; H, 4.51; N, 9.35; S, 10.90; F, 6.21.

What is claimed is:

1. A compound having the formula

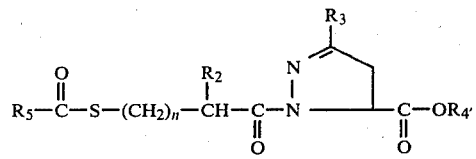

or a non-toxic, physiologically acceptable basic salt thereof, where
   $R_2$ is hydrogen or alkyl;
   $R_3$ is aryl;
   $R_4$ is hydrogen, alkyl or arylalkyl;
   $R_5$ is alkyl or aryl; and
   n is 0, 1 or 2;
wherein the term "aryl" refers to phenyl or phenyl substituted with one, two or three halogen, alkyl, alkoxy, hydroxy,

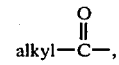

nitro, amino, alkylamino, dialkylamino, trifluoromethyl, cyano or carboxyl groups, and the terms "alkyl" and "alkoxy" refer to groups having 1 to 8 carbon atoms.

2. A compound in accordance with claim 1 wherein $R_2$ is hydrogen.
3. A compound in accordance with claim 1 wherein $R_2$ is methyl.
4. A compound is accordance with claim 1 wherein $R_4$ is hydrogen.
5. A compound in accordance with claim 1 wherein $R_4$ is alkyl.
6. A compound in accordance with claim 1 wherein $R_4$ is arylalkyl.
7. A compound in accordance with claim 1 wherein n is O.
8. A compound in accordance with claim 1 wherein n is 1.
9. A compound in accordance with claim 1 wherein n is 2.

10. The compound in accordance with claim 1 DL-4,5-dihydro-1-[3-(acetylthio)-1-oxopropyl]-3-phenyl-1H-pyrazole-5-carboxylic acid.

11. The compound in accordance with claim 1, DL-3-(4-chlorophenyl)-4,5-dihydro-1-[3-(acetylthio)-1-oxopropyl]-1H-pyrazole-5-carboxylic acid.

12. The compound in accordance with claim 1, D,L-3-(4-methoxyphenyl)-4,5-dihydro-1-[3-(acetylthio)-1-oxopropyl]-1H-pyrazole-5-carboxylic acid.

13. The compound in accordance with claim 1, D,L-3-(4-fluorophenyl)-4,5-dihydro-1-[3-(acetylthio)-1-oxopropyl]-1H-pyrazole-5-carboxylic acid.

14. A method for reducing blood pressure in mammals which comprises administering to a mammal in need thereof, an effective amount of a compound having the formula

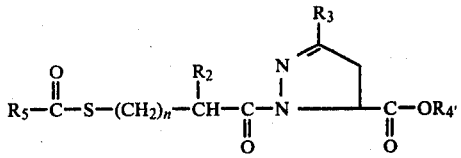

or a non-toxic, physiologically acceptable basic salt thereof, wherein
  $R_2$ is hydrogen or alkyl;
  $R_3$ is aryl;
  $R_4$ is hydrogen, alkyl or arylalkyl;
  $R_5$ is alkyl or aryl; and
  n is 0, 1 or 2;
wherein the term "aryl" refers to phenyl or phenyl substituted with one, two three halogen, alkyl, alkoxy, hydroxy,

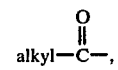

nitro, amino, alkylamino, dialkylamino, trifluoromethyl, cyano or carboxyl groups, and the terms "alkyl" and "alkoxy" refer to groups having 1 to 8 carbon atoms.

* * * * *

UNITED STATES PATENT OFFICE
CERTIFICATE OF CORRECTION

Patent No. 4,221,804  Dated September 9, 1980

Inventor(s) George C. Rovnyak

It is certified that error appears in the above-identified patent and that said Letters Patent are hereby corrected as shown below:

Column 2, line 56, ╪halogen" should read --"halogen"--

Column 2, line 67, "or" should read --on--

Column 5, line 38, "wit" should read --with--

Claim 1, column 8, line 35, "where" should read --wherein--

Claim 14, column 10, line 17, insert "or" between "two three"

Signed and Sealed this

Third Day of February 1981

[SEAL]

Attest:

RENE D. TEGTMEYER

Attesting Officer  Acting Commissioner of Patents and Trademarks